US008501738B2

(12) United States Patent
Harbeson et al.

(10) Patent No.: US 8,501,738 B2
(45) Date of Patent: Aug. 6, 2013

(54) SUBSTITUTED TRIAZOLO-PYRIDAZINE DERIVATIVES

(75) Inventors: Scott L. Harbeson, Cambridge, MA (US); Julie F. Liu, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 12/820,570

(22) Filed: Jun. 22, 2010

(65) Prior Publication Data
US 2011/0065711 A1 Mar. 17, 2011

Related U.S. Application Data

(60) Provisional application No. 61/269,332, filed on Jun. 23, 2009.

(51) Int. Cl.
A01N 43/58 (2006.01)
A61K 31/50 (2006.01)
C07D 487/00 (2006.01)

(52) U.S. Cl.
USPC .......................................... 514/248; 544/236

(58) Field of Classification Search
USPC .......................................... 544/236; 514/248
See application file for complete search history.

(56) References Cited

U.S. PATENT DOCUMENTS

| | | | |
|---|---|---|---|
| 6,221,335 | B1 | 4/2001 | Foster |
| 6,440,710 | B1 | 8/2002 | Keinan et al. |
| 6,603,008 | B1 | 8/2003 | Ando et al. |
| 6,630,471 | B1 | 10/2003 | Carling et al. |
| 7,517,990 | B2 | 4/2009 | Ito et al. |
| 8,003,646 | B2 | 8/2011 | Harbeson |
| 2007/0082929 | A1 | 4/2007 | Gant et al. |
| 2007/0197695 | A1 | 8/2007 | Potyen et al. |
| 2008/0103122 | A1 | 5/2008 | Veltri |
| 2012/0004236 | A1 | 1/2012 | Harbeson |

FOREIGN PATENT DOCUMENTS

| | | |
|---|---|---|
| WO | WO 95/26325 A2 | 10/1995 |
| WO | WO 98/04559 A2 | 2/1998 |
| WO | WO 99/67245 A1 | 12/1999 |
| WO | WO 00/44752 A1 | 8/2000 |
| WO | WO 2006/061428 A2 | 6/2006 |
| WO | WO 2007/118651 A1 | 10/2007 |
| WO | WO 2010/025407 A1 | 3/2010 |
| WO | WO 2011/005520 A1 | 1/2011 |

OTHER PUBLICATIONS

Atack et al, Knabl et al.*
Mathiasen et al.*
Ma, B., et al., "Cytochrome P450 3A-Dependent Metabolism of a Potent and Selective γ-Aminobutyric Acid$_{A\alpha2/3}$ Receptor Agonist in Vitro: Involvement of Cytochrome P450 3A5 Displaying Biphasic Kinetics," DMD 35(8):1301-1307 (2007).

Polsky-Fisher, S.L., et al., "Metabolism and Disposition of a Potent and Selective GABA-A$_{\alpha2/3}$ Receptor Agonist in Healthy Male Volunteers," DMD 34(6):1004-1011 (2006).
Notification of Transmittal of the International Search Report and the Written Opinion of the International Searching Authority, or the Declaration, International Application No. PCT/US2010/039497, Date of mailing: Oct. 13, 2010.
Baille, T. A., "The Use of Stable Isotopes in Pharmacological Research," Pharmacological Reviews, 33(2): 81-132 (1981).
Browne, T. R., "Stable Isotope Techniques in Early Drug Development: An Economic Evaluation," J. Clin. Pharmacol., 38: 213-220 (1998).
Cherrah, Y., et al., "Study of Deuterium Isotope Effects on Protein Binding by Gas Chromatography/Mass Spectrometry. Caffeine and Deuterated Isotopomers," Biomedical and Environmental Mass Spectrometry, 14: 653-657 (1987).
de Haas, S. L. et al., "Pharmacodynamic and Pharmacokinetic Effects of TPA023, a GABA$_A$ $\alpha_{2,3}$ Subtype-Selective Agonist, Compared to Lorazepam and Placebo in Healthy Volunteers," Journal of Psychopharmacology, 21(4): 374-383 (2007).
Dyck, L. E., et al., "Effects of Deuterium Substitution on the Catabolism of β-Phenylethylamine: An in Vivo Study," Journal of Neurochemistry, 46(2): 399-404 (1986).
Fisher, M.B. et al., "The Complexities Inherent in Attempts to Decrease Drug Clearance by Blocking Sites of CYP-Mediated Metabolism," Curr. Opin. Drug Discov. Devel., 9(1):101-109 (2006).
Foster, A. B., "Deuterium Isotope Effects in Studies of Drug Metabolism," Trends in Pharmacological Sciences, 5: 524-527 (1984).
Foster, A. B., "Deuterium Isotope Effects in the Metabolism of Drugs and Xenobiotics: Implications for Drug Design," Advances in Drug Research, 14: 1-40 (1985).
Gouyette, A., "Synthesis of Deuterium-labelled Elliptinium and its Use in Metabolic Studies," Biomedical and Environmental Mass Spectrometry, 15: 243-247 (1988).
Haskins, N. J., "The Application of Stable Isotopes in Biomedical Research," Biomedical Mass Spectrometry, 9(7): 269-277 (1982).
Honma S., et al., "The Metabolism of Roxatidine Acetate Hydrochloride," Drug Metabolism and Disposition, 15(4): 551-559 (1987).
Kushner, D.J. et al., "Pharmacological Uses and Perspectives of Heavy Water and Deuterated Compounds," Can. J. Physiol. Pharmacol., 77:79-88 (1999).
Pieniaszek, H. J., et al., "Moricizine Bioavailability via Simultaneous, Dual, Stable Isotope Administration: Bioequivalence Implications," J. Clin. Pharmacol, 39: 817-825 (1999).
Tonn G. R., et al., "Simultaneous Analysis of Diphenhydramine and a Stable Isotope Analog ($^2$H$_{10}$) Diphenhydramine Using Capillary Gas Chromatography with Mass Selective Detection in Biological Fluids from Chronically Instrumented Pregnant Ewes," Biological Mass Spectrometry, 22: 633-642 (1993).
Wolen, R. L., "The Application of Stable Isotopes to Studies of Drug Bioavailability and Bioequivalence," J. Clin. Pharmacol., 26: 419-424 (1986).

* cited by examiner

Primary Examiner — Paul V. Ward
(74) Attorney, Agent, or Firm — Edwards Wildman Palmer LLP; Jeffrey D. Hsi; Mark D. Russett

(57) ABSTRACT

This invention relates to novel substituted triazolo-pyridazines and pharmaceutically acceptable salts thereof. This invention also provides compositions comprising a compound of this invention and the use of such compositions in methods of treating diseases and conditions that are beneficially treated by administering an α1-GABA$_A$ receptor antagonist or an α2- and/or an α3-GABA$_A$ receptor partial agonist.

16 Claims, 2 Drawing Sheets

SUBSTITUTED TRIAZOLO-PYRIDAZINE DERIVATIVES

RELATED APPLICATION

This application claims the benefit of U.S. Provisional Application No. 61/269,332, filed on Jun. 23, 2009. The entire teachings of the above application are incorporated herein by reference.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor subject compliance with the dosing regimen, side effects that become more acute with higher doses, and increased cost of treatment. A rapidly metabolized drug may also expose subjects to undesirable toxic or reactive metabolites.

Another ADME limitation that affects many medicines is the formation of toxic or biologically reactive metabolites. As a result, some subjects receiving the drug may experience toxicities, or the safe dosing of such drugs may be limited such that subjects receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV subjects who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56 (6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

SUMMARY OF THE INVENTION

This invention relates to novel substituted triazolo-pyridazines and pharmaceutically acceptable salts thereof. $GABA_A$ receptors are ligand-gated chloride channels that mediate the inhibitory effects of γ-aminobutyric acid (GABA) in the CNS. $GABA_A$ receptors are heteromeric proteins of five subunits primarily found as receptors containing α, β, and γ subunits in a 2:2:1 stoichiometry. $GABA_A$ receptors containing the α1, α2, α3, or α5 subunits contain a binding site for benzodiazepines, which is the basis for the pharmacologic activity of benzodiazepines. This invention also provides compositions comprising a compound of this invention and the use of such compositions in methods of treating diseases and conditions that are beneficially treated by administering an antagonist for $GABA_A$ receptors at the benzodiazepine site consisting of an α1 subunit or a partial agonist for $GABA_A$ receptors at the benzodiazepine site containing an α2 or α3 subunit.

TPA-023, also known as 7-tert-Butyl-6-(1-ethyl-1H-1,2,4-triazol-5-ylmethoxy)-3-(2-fluorophenyl)-1,2,4-triazolo[4,3-b]pyridazine, and as 7(1,1-dimethylethyl)-6-(2-ethyl-2H-1,2,4-triazol-3-ylmethoxy)-3-(2-fluorophenyl)-1,2,4-triazolo[4,3-b]pyridazine, is a selective ligand for $GABA_A$ receptors, which antagonizes the α1 subunit, and is a partial agonist of the α2 and α3 subunits.

TPA-023 has been analyzed in humans in a phase I clinical trial (de Haas S L, et al, J Psychopharmacol, 2007, 21(4):374-83). It demonstrated anxiolytic effects, with no effect on alertness, muscle relaxation or memory. It also demonstrated sedative effects at certain doses tested. Compounds exhibiting a $GABA_A$ receptor profile similar to TPA-023 have also shown activity in pharmacological models of both inflammatory and neuropathic pain.

Despite the purported beneficial activities of TPA-023, there is a continuing need for new compounds that are anxiolytic without concomitant sedative effects. Additionally, there is a need for new antinociceptive agents with activity in inflammatory and/or neuropathic pain.

DETAILED DESCRIPTION OF THE INVENTION

Figure 1:
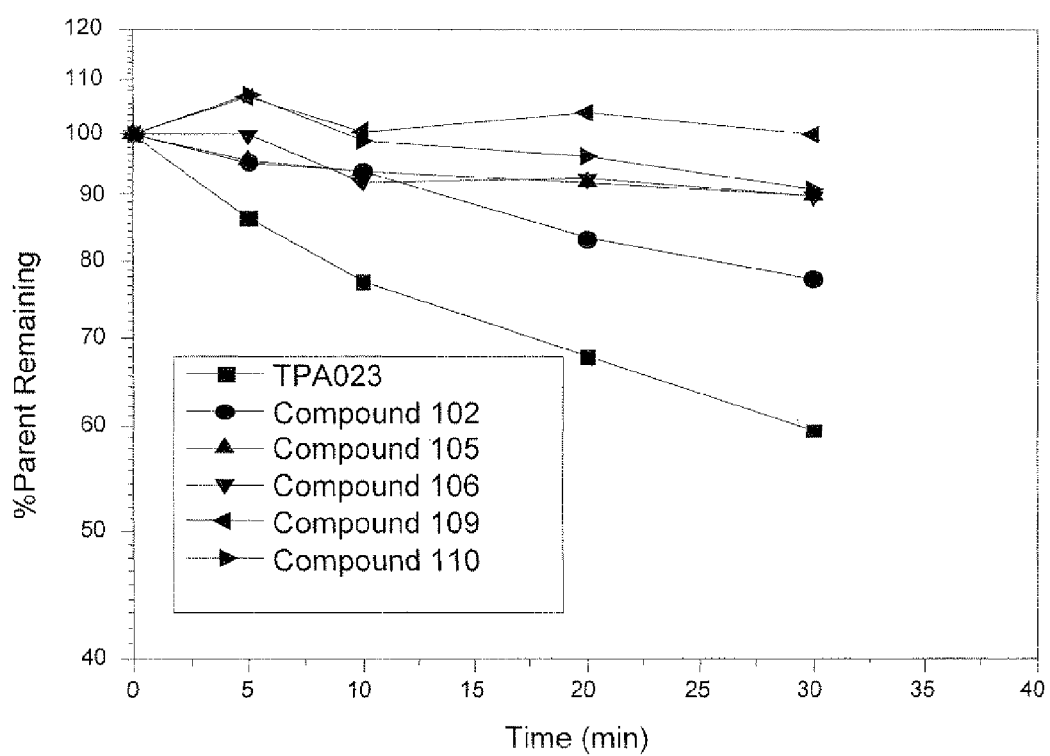
FIG. 1 depicts the time course of disappearance of certain compounds of the invention during incubation with human liver microsomes.

The term "treat" means decrease, suppress, attenuate, diminish, arrest, or stabilize the development or progression of a disease (e.g., a disease or disorder delineated herein).

"Disease" means any condition or disorder that damages or interferes with the normal function of a cell, tissue, or organ.

"The term "alkyl" refers to a monovalent saturated hydrocarbon group. $C_1$-$C_6$ alkyl is an alkyl having from 1 to 6 carbon atoms. An alkyl may be linear or branched. Examples of alkyl groups include methyl; ethyl; propyl, including n-propyl and isopropyl; butyl, including n-butyl, isobutyl, sec-butyl, and t-butyl; pentyl, including, for example, n-pentyl, isopentyl, and neopentyl; and hexyl, including, for example, n-hexyl and 2-methylpentyl.

It will be recognized that some variation of natural isotopic abundance occurs in a synthesized compound depending upon the origin of chemical materials used in the synthesis. Thus, a preparation of TPA-023 will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada E et al., Seikagaku 1994, 66:15; Gannes L Z et al., Comp Biochem Physiol Mol Integr Physiol 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in two will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free of another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium. "Stereoisomer" refers to both enantiomers and diastereomers. "Tert", """, and "t-" each refer to tertiary. "US" refers to the United States of America.

The term "substituted with deuterium" means that one or more hydrogen atoms in the indicated moiety are replaced with a corresponding number of deuterium atoms.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula I:

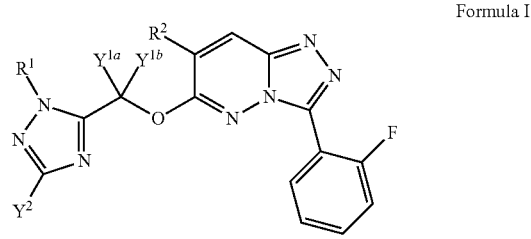

Formula I or a pharmaceutically acceptable salt thereof, wherein:

$R^1$ is —$CH_3$ or —$CH_2CH_3$, wherein $R^1$ is optionally substituted with deuterium;

$R^2$ is (a) —$C_1$-$C_6$ alkyl optionally substituted with one or two Z, wherein Z is selected from:

—$CH_3$ optionally substituted with deuterium; halogen; and —OH;

(b) —$OC_1$-$C_6$ alkyl;

(c) —C(O)H;

(d) —C(O)$C_1$-$C_6$ alkyl;

(e) —C(O)O$C_1$-$C_6$ alkyl; or (f) —$CR^5$=$NOR^4$, wherein each alkyl in $R^2$ is optionally substituted with one or more deuterium;

$R^5$ is selected from hydrogen, deuterium, and $C_1$-$C_6$ alkyl optionally substituted with one or more deuterium;

$R^4$ is $C_1$-$C_6$ alkyl optionally substituted with hydroxyl or with —N($C_1$-$C_6$ alkyl)$_2$ wherein each alkyl in $R^4$ is optionally substituted with deuterium;

each $Y^1$ is independently hydrogen or deuterium; and $Y^2$ is hydrogen or deuterium;

with the proviso that when $R^1$ is unsubstituted —$CH_3$ or unsubstituted —$CH_2CH_3$; Z is unsubstituted —$CH_3$; $R^2$ is not substituted with deuterium; $R^5$ is hydrogen or $C_1$-$C_6$ alkyl not substituted with deuterium; and $R^4$ is not substituted with deuterium;

then at least one of $Y^1$ and $Y^2$ is deuterium.

In one embodiment, $R^2$ is methyl, fluoromethyl, difluoromethyl, hydroxymethyl, hydroxyethyl, difluoroethyl, fluoropropyl, hydroxypropyl, t-butyl, O-methyl, —C(O)H, —C(O)methyl, -carbonyloxymethyl and —$CR^5$=$NOR^4$, wherein each alkyl in $R^2$ is optionally substituted with one or more deuterium. In an example of this embodiment, $R^2$ is selected from —$CH_3$, —$CD_3$, —$CF_2CH_3$, —$CF_2CD_3$, —$CF(CH_3)_2$, —$CF(CD_3)_2$, —$C(OH)(CH_3)_2$, —$C(OH)(CD_3)_2$, —$C(CH_3)_3$, and —$C(CD_3)_3$.

In one embodiment, $R^5$ is selected from hydrogen, deuterium, $CH_3$, and $CD_3$.

In one embodiment, $R^4$ is selected from methyl, ethyl, hydroxyethyl, and dimethylaminoethyl wherein each alkyl in $R^4$ is optionally substituted with deuterium.

In one embodiment, $R^2$ is methyl, fluoromethyl, difluoromethyl, hydroxymethyl, hydroxyethyl, difluoroethyl, fluoropropyl, hydroxypropyl, t-butyl, O-methyl, —C(O)H, —C(O)methyl, -carbonyloxymethyl and —$CR^5$=$NOR^4$, wherein each alkyl in $R^2$ is optionally substituted with one or more deuterium;

$R^5$ is selected from hydrogen, deuterium, $CH_3$, and $CD_3$; and $R^4$ is selected from methyl, ethyl, hydroxyethyl, and dimethylaminoethyl wherein each alkyl in $R^4$ is optionally substituted with deuterium. In an example of this embodiment, $R^2$ is selected from —$CH_3$, —$CD_3$, —$CF_2CH_3$, —$CF(CH_3)_2$, —$CF(CH_3)_2$, —$CF(CD_3)_2$, —$C(OH)(CH_3)_2$, —$C(OH)(CD_3)_2$, —$C(CH_3)_3$, and —$C(CD_3)_3$.

One embodiment of this invention provides a compound of formula Ia

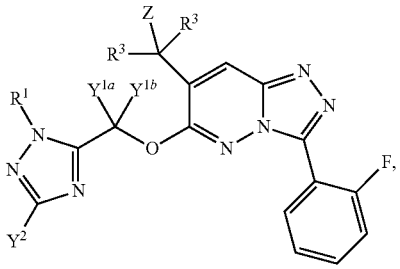

(Ia)

or a pharmaceutically acceptable salt thereof, wherein:
R$^1$ is —CH$_3$, or —CH$_2$CH$_3$, wherein R$^1$ is optionally substituted with deuterium;
Z is —OH or —CH$_3$, wherein the —CH$_3$ of Z is optionally substituted with deuterium;
each R$^3$ is —CH$_3$ wherein each R$^3$ is optionally substituted with deuterium;
each Y$^1$ is independently hydrogen or deuterium; and
Y$^2$ is hydrogen or deuterium,
with the proviso that when R$^1$ is unsubstituted —CH$_3$ or unsubstituted —CH$_2$CH$_3$; each R$^3$ is unsubstituted —CH$_3$; and Z is unsubstituted —CH$_3$; then at least one of Y$^1$ and Y$^2$ is deuterium.

One embodiment of this invention provides a compound of Formula Ia, wherein —CZ(R$^3$)$_2$ is —C(CH$_3$)$_3$ or —C(CD$_3$)$_3$ and Y$^{1a}$ and Y$^{1b}$ are the same. In one aspect of this embodiment, Y$^{1a}$ and Y$^{1b}$ are hydrogen. In another aspect, Y$^{1a}$ and Y$^{1b}$ are deuterium. In another aspect, Y$^2$ is hydrogen. In another aspect, Y$^2$ is deuterium.

One embodiment of this invention provides a compound of Formula Ia, wherein R$^1$ is —CH$_3$, —CD$_3$, —CH$_2$CH$_3$, —CD$_2$CH$_3$, —CH$_2$CD$_3$, or —CD$_2$CD$_3$. In one aspect of this embodiment, R$^1$ is —CH$_2$CH$_3$, —CD$_2$CH$_3$, —CH$_2$CD$_3$, or —CD$_2$CD$_3$. In another aspect, Y$^{1a}$ and Y$^{1b}$ are hydrogen. In another aspect, Y$^{1a}$ and Y$^{1b}$ are deuterium. In another aspect, Y$^2$ is hydrogen. In another aspect, —CZ(R$^3$)$_2$ is —C(CH$_3$)$_3$ or —C(CD$_3$)$_3$. In still another aspect, —CZ(R$^3$)$_2$ is —C(CD$_3$)$_3$. In yet another aspect, R$^1$ is —CH$_2$CH$_3$, —CD$_2$CH$_3$, —CH$_2$CD$_3$, or —CD$_2$CD$_3$; Y$^{1a}$ and Y$^{1b}$ are the same; Y$^2$ is hydrogen; and —CZ(R$^3$)$_2$ is —C(CH$_3$)$_3$ or —C(CD$_3$)$_3$.

One embodiment provides compounds of Formula Ia, wherein —CZ(R$^3$)$_2$ is —C(CH$_3$)$_3$ or —C(CD$_3$)$_3$.

One embodiment provides compounds of Formula Ia, wherein —CZ(R$^3$)$_2$ is —C(OH)(CD$_3$)$_2$.

One embodiment provides compounds of Formula Ia, wherein —CZ(R$^3$)$_2$ is —C(OH)(CH$_3$)$_2$.

One embodiment provides compounds of Formula Ia, wherein Y$^{1a}$ and Y$^{1b}$ are the same and Y$^2$ is hydrogen. In one aspect of this embodiment, —CZ(R$^3$)$_2$ is —C(CD$_3$)$_3$. In another aspect of this embodiment, Y$^{1a}$ and Y$^{1b}$ are deuterium. In still another aspect, —CZ(R$^3$)$_2$ is —C(CD$_3$)$_3$; and Y$^{1a}$ and Y$^{1b}$ are deuterium.

In one embodiment of a compound of formula, Y$^2$ is hydrogen; —CZ(R$^3$)$_2$ is —C(CD$_3$)$_3$; and the compound is selected from any one of the compounds set forth in Table 1 below.

TABLE 1

Examples of Compounds of Formula Ia

| Compound | R$^1$ | Y$^{1a}$ | Y$^{1b}$ |
|---|---|---|---|
| 101 | CH$_2$CH$_3$ | D | D |
| 102 | CH$_2$CH$_3$ | H | H |

TABLE 1-continued

Examples of Compounds of Formula Ia

| Compound | R$^1$ | Y$^{1a}$ | Y$^{1b}$ |
|---|---|---|---|
| 103 | CH$_2$CD$_3$ | H | H |
| 104 | CH$_2$CD$_3$ | D | D |
| 105 | CD$_2$CD$_3$ | H | H |
| 106 | CD$_2$CD$_3$ | D | D |
| 107 | CD$_2$CH$_3$ | H | H |
| 108 | CD$_2$CH$_3$ | D | D | or a pharmaceutically acceptable salt of any of the foregoing.

In one embodiment of a compound of formula Ia, Y$^2$ is hydrogen; —CZ(R$^3$)$_2$ is —C(CD$_3$)$_3$; R$^1$ is —CD$_3$; and Y$^{1a}$ and Y$^{1b}$ are each hydrogen:

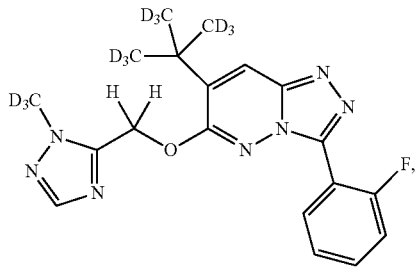

109 or a pharmaceutically acceptable salt of the foregoing.

In one embodiment of a compound of formula Ia, Y$^2$ is hydrogen; —CZ(R$^3$)$_2$ is —C(CD$_3$)$_3$; R$^1$ is CD$_3$; and Y$^{1a}$ and Y$^{1b}$ are each deuterium:

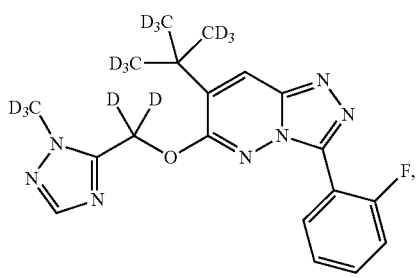

110 or a pharmaceutically acceptable salt of the foregoing.

In one embodiment of a compound of formula Ia, Y$^2$ is hydrogen; —CZ(R$^3$)$_2$ is

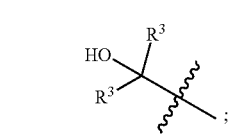

and the compound is selected from any one of the compounds set forth in Table 2 below.

TABLE 2

Examples of Compounds of Formula Ia

| Compound | $R^1$ | $R^3$ | $Y^{1a}$ | $Y^{1b}$ |
|---|---|---|---|---|
| 201 | $CH_2CH_3$ | $CD_3$ | D | D |
| 202 | $CH_2CH_3$ | $CD_3$ | H | H |
| 203 | $CH_2CD_3$ | $CD_3$ | H | H |
| 204 | $CH_2CD_3$ | $CD_3$ | D | D |
| 205 | $CD_2CD_3$ | $CD_3$ | H | H |
| 206 | $CD_2CD_3$ | $CD_3$ | D | D |
| 207 | $CD_2CH_3$ | $CD_3$ | H | H |
| 208 | $CD_2CH_3$ | $CD_3$ | D | D |
| 209 | $CH_2CH_3$ | $CH_3$ | D | D |
| 210 | $CH_2CH_3$ | $CH_3$ | H | H |
| 211 | $CH_2CD_3$ | $CH_3$ | H | H |
| 212 | $CH_2CD_3$ | $CH_3$ | D | D |
| 213 | $CD_2CD_3$ | $CH_3$ | H | H |
| 214 | $CD_2CD_3$ | $CH_3$ | D | D |
| 215 | $CD_2CH_3$ | $CH_3$ | H | H |
| 216 | $CD_2CH_3$ | $CH_3$ | D | D | or a pharmaceutically acceptable salt of any of the foregoing.

The present invention also provides a compound of Formula II:

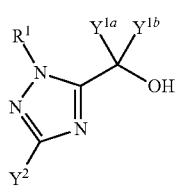

Formula II or a salt thereof, such as a pharmaceutically acceptable salt thereof, wherein:

$R^1$, each $Y^1$ and $Y^2$ are as defined above for Formula I, provided that when $R^1$ is unsubstituted —$CH_3$ or unsubstituted —$CH_2CH_3$ and each $Y^1$ is hydrogen, then $Y^2$ is deuterium.

In one embodiment, $Y^2$ is hydrogen; $R^1$ is $CD_3$; and $Y^{1a}$ nd $Y^{1b}$ are each deuterium:

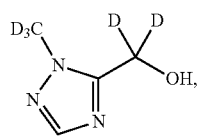

301 or a pharmaceutically acceptable salt thereof.

In one embodiment, $Y^2$ is hydrogen; $R^1$ is $CD_2CD_3$; and $Y^{1a}$ and $Y^{1b}$ are each deuterium:

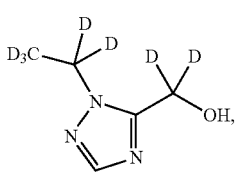

302 or a pharmaceutically acceptable salt thereof.

In another set of embodiments, any atom not designated as deuterium in any of the embodiments set forth above is present at its natural isotopic abundance.

The synthesis of compounds of Formula I can be readily achieved by synthetic chemists of ordinary skill by reference to the Exemplary Synthesis and Examples disclosed herein.

Exemplary Synthesis

Compounds of Formula I can be prepared according to the schemes shown below.

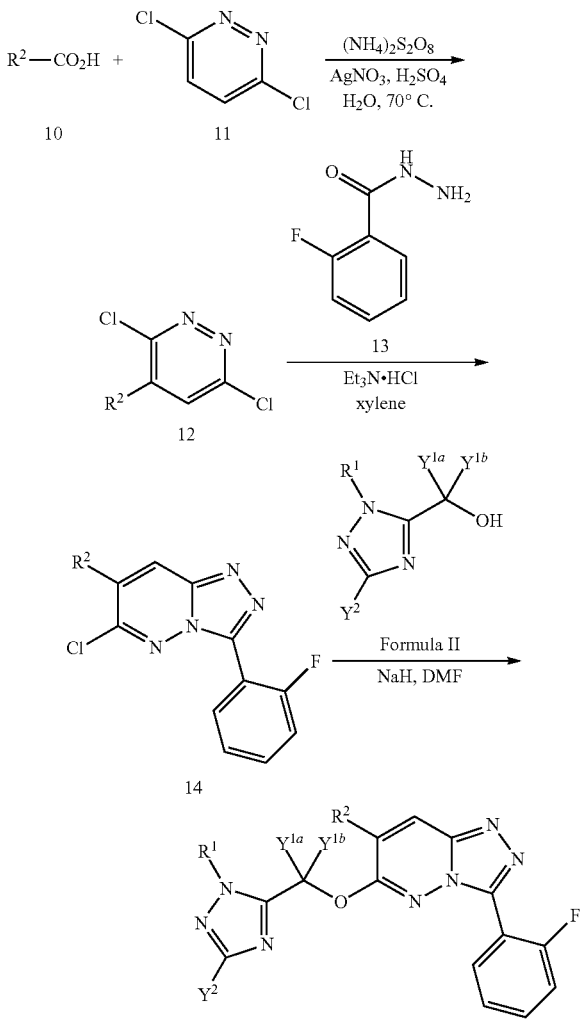

Scheme 1. General Route to Compounds of Formula I, wherein $R^2$ is —$C(CH_3)_3$ Optionally Substituted with Deuterium.

Formula I Wherein $R^2$ is —$C(CH_3)_3$ Optionally Substituted with Deuterium

The synthesis of compounds of Formula I, wherein $R^2$ is —$C(CH_3)_3$ optionally substituted with deuterium, can be accomplished generally as shown in Scheme 1. Intermediate 12 is prepared by radical alkylation of 3,6-dichloropyridazine 11 with the appropriately deuterated pivalic acid 10. D9-Pivalic acid is commercially available for the preparation of those compounds wherein $R^2$ is —$C(CD_3)_3$. The appropriately deuterated 3,6-dichloro-4-t-butylpyridazine 12 is then condensed with commercially available 2-fluorobenzohydrazide (13) to provide 14. Displacement of the chloride with the anion generated from Formula II and NaH provides compounds of Formula I, wherein $R^2$ is —$C(CH_3)_3$ optionally substituted with deuterium.

Scheme 2. Synthesis of Compounds of Formula II.

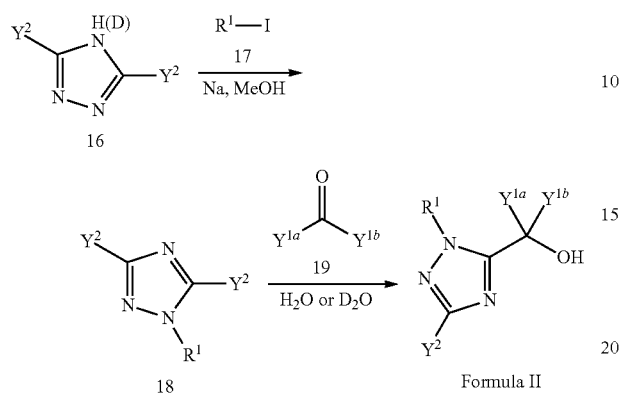

Scheme 2 illustrates the preparation of deuterated analogs of Formula II. As generally described by Dallacker F et al, Chemiker-Zeitung 1986, 110:101-108 and Dallacker F et al, Chemiker-Zeitung 1986, 110, p. 275-281, commercially available 1,2,4-triazole (16) (or commercially available 1,2,4-triazole-d3) is reacted with $R^1$—I 17 to provide the appropriately deuterated methyl triazole 18, which is then treated with formaldehyde or deuterated formaldehyde 19 to provide a compound of Formula II. $CD_3$-I, $CH_3CD_2$-I, $CD_3CH_2$—I, and $CD_3CD_2$-I are all commercially available.

Scheme 3: General Route to Compounds of Formula I, wherein $R^2$ is

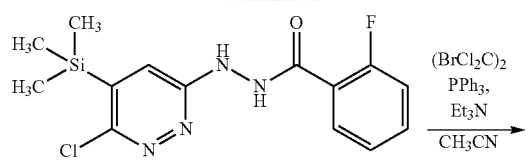

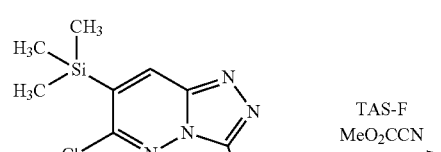

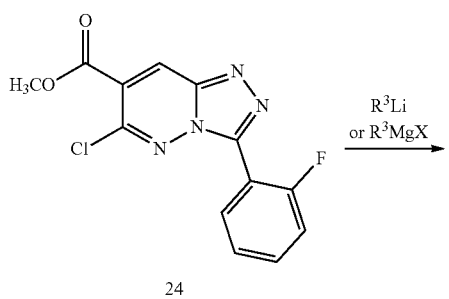

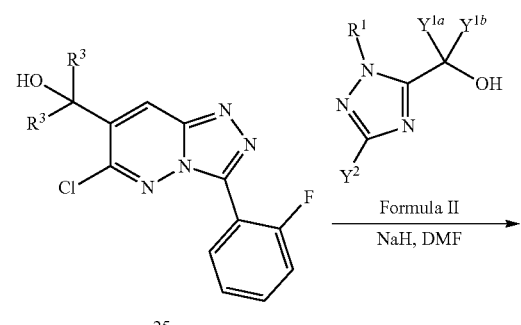

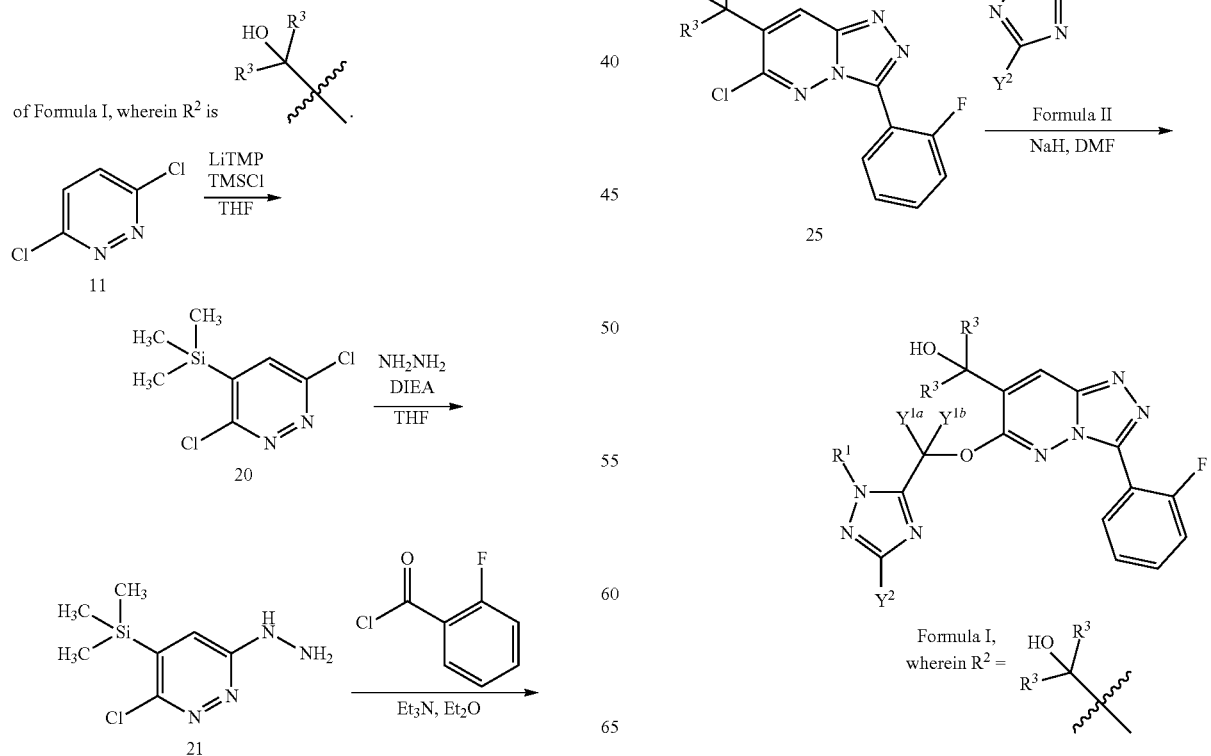

Scheme 3 depicts the preparation of compounds of Formula I, wherein $R^2$ is

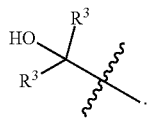

Following the general methods described in Collins, et al.; Tet. Lett. 2000, 41, 781-784, commercially-available 3,6-dichloropyridazine 11 is treated with lithium tetramethylpiperidide (LiTMP) and trimethylsilyl chloride (TMSCl) to afford compound 20. Treatment with anhydrous hydrazine provides amine 21, and acylation with commercially-available 2-fluorobenzoyl chloride affords 22. Cyclization via treatment with triphenylphosphonium dibromide, generated in situ from triphenylphosphine and 1,2-dibromotetrachloroethane, provides bicycle 23. Treatment with tris(dimethylamino)sulfonium difluorotrimethylsilicate (TAS-F) and methyl cyanoformate yields ester 24. Treatment with the appropriate alkyl lithium reagent or Grignard reagent, wherein X is chloride, bromide or iodide, provides alcohol 25. Alternatively, compound 23 may be converted directly to compound 25 following the general methods disclosed in WO 1999037644, via treatment with tetrabutylammonium difluorotriphenylstannate and appropriately-deuterated acetone. Displacement of the chloride of compound 25 with the anion of a compound of Formula II provides compounds of Formula I, wherein $R^2$ is

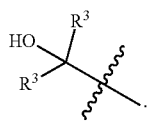

In one example, commercially-available methyl-d3-lithium or methyl-d3-magnesium iodide may be used in Scheme 3 to ultimately provide compounds of Formula I wherein $R^3$ is $CD_3$.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Combinations of substituents and variables envisioned by this invention are only those that result in the formation of stable compounds.

Compositions

The invention also provides pyrogen-free compositions comprising an effective amount of a compound of Formula I (e.g., including any of the formulae herein), or a pharmaceutically acceptable salt of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Inform Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the subject, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound that either antagonizes the α1 subunit of $GABA_A$ receptors, or which is a partial agonist of the α2 and/or α3 subunits of $GABA_A$ receptors.

Preferably, the second therapeutic agent is an agent useful in the treatment or prevention of a disease or condition selected from anxiety, convulsions, skeletal muscle spasm, spasticity, athetosis, epilepsy, stiff-person syndrome, other disorders of the central nervous system, and pain.

Examples of pain include acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, and cancer pain. More particular examples include femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, including abdominal, pancreatic, and IBS pain; chronic and acute headache pain; migraine; tension headache, including cluster headaches; chronic and acute neuropathic pain, including post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including abdominal pain, pyelonephritis, appendicitis, cholecystitis, intestinal obstruction, and hernias; chest pain, including cardiac pain; pelvic pain; renal colic pain; acute obstetric pain, including labor pain; cesarean section pain; acute inflammatory, burn and trauma pain; acute intermittent pain, including endometriosis; acute herpes zoster pain; sickle cell anemia; acute pancreatitis; breakthrough pain; orofacial pain including sinusitis pain and dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; painful bladder syndrome; interstitial cystitis (IC); prostatitis; complex regional pain syndrome (CRPS), type I and type II; and angina-induced pain. For example, the pain may be pain selected from the group consisting of fibromyalgia, acute herpes zoster pain, HIV-associated neuropathy, neuropathic low back pain, chemotherapy induced neuropathic pain, radiotherapy-induced neuropathic pain, peripheral nerve injury, spinal cord injury pain, and multiple sclerosis (MS) pain.

In one embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention can range from about 0.01 to about 5000 mg per treatment. In more specific embodiments the range is from about 0.1 to 2500 mg, or from 0.2 to 1000 mg, or most specifically from about 1 to 500 mg. Treatment typically is administered one to three times daily.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2" Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to another embodiment, the invention provides a method of treating a subject suffering from, or susceptible to, a disease that is beneficially treated by a $α1\text{-}GABA_A$ receptor antagonist or an α2- and/or an $α3\text{-}GABA_A$ receptor partial agonist, comprising the step of administering to said subject an effective amount of a compound of this invention or a pharmaceutically acceptable salt of said compound or a composition of this invention. As an example, the subject may be a human patient.

Such diseases are well known in the art and are disclosed in, but not limited to the following patents and published applications: WO 1998004559, WO 2000044752, WO 2006061428 and U.S. Pat. No. 6,630,471. Such diseases include, but are not limited to, anxiety, convulsions, skeletal muscle spasm, spasticity, athetosis, epilepsy, stiff-person syndrome, other disorders of the central nervous system, and pain (e.g., neuropathic pain, inflammatory pain, and migraine-associated pain). In a particular embodiment, the disease is selected from anxiety and convulsions.

In one embodiment, the disease is pain selected from the group consisting of: acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head pain, neck pain, severe or intractable pain, nociceptive pain, breakthrough pain, postsurgical pain, and cancer pain.

In another embodiment, the pain is selected from the group consisting of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, including abdominal, pancreatic, and IBS pain; chronic and acute headache pain; migraine; tension headache, including cluster headaches; chronic and acute neuropathic pain, including post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including abdominal pain, pyelonephritis, appendicitis, cholecystitis, intestinal obstruction, and hernias; chest pain, including cardiac pain; pelvic pain; renal colic pain; acute obstetric pain, including labor pain; cesarean section pain; acute inflammatory, burn and trauma pain; acute intermittent pain, including endometriosis; acute herpes zoster pain; sickle cell anemia; acute pancreatitis; breakthrough pain; orofacial pain including sinusitis pain and dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; painful bladder syndrome; interstitial cystitis (IC); prostatitis; complex regional pain syndrome (CRPS), type I and type II; and angina-induced pain.

In yet another embodiment, the pain is selected from the group consisting of: fibromyalgia, acute herpes zoster pain, HIV-associated neuropathy, neuropathic low back pain, chemotherapy induced neuropathic pain, radiotherapy-induced neuropathic pain, peripheral nerve injury, spinal cord injury pain, and multiple sclerosis (MS) pain.

Methods delineated herein also include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In another embodiment, any of the above methods of treatment comprises the further step of co-administering to the subject one or more second therapeutic agents. The choice of second therapeutic agent may be made from any second therapeutic agent known to be useful for co-administration with a compound that either antagonizes the α1 subunit of $GABA_A$ receptors, or which is a partial agonist of the α2 and/or α3 subunits of $GABA_A$ receptors. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I, or a pharmaceutically acceptable salt of said compound, alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of Formula I for use in the treatment or prevention in a subject of a disease, disorder or symptom thereof delineated herein.

EXAMPLES

Example 1

Synthesis of 7-$d_9$-tert-Butyl-6-((1-ethyl-1H-1,2,4-triazol-5-yl)methoxy)-3-(2-fluorophenyl)-1,2,41-triazolo[4,3-b]pyridazine (Compound 102)

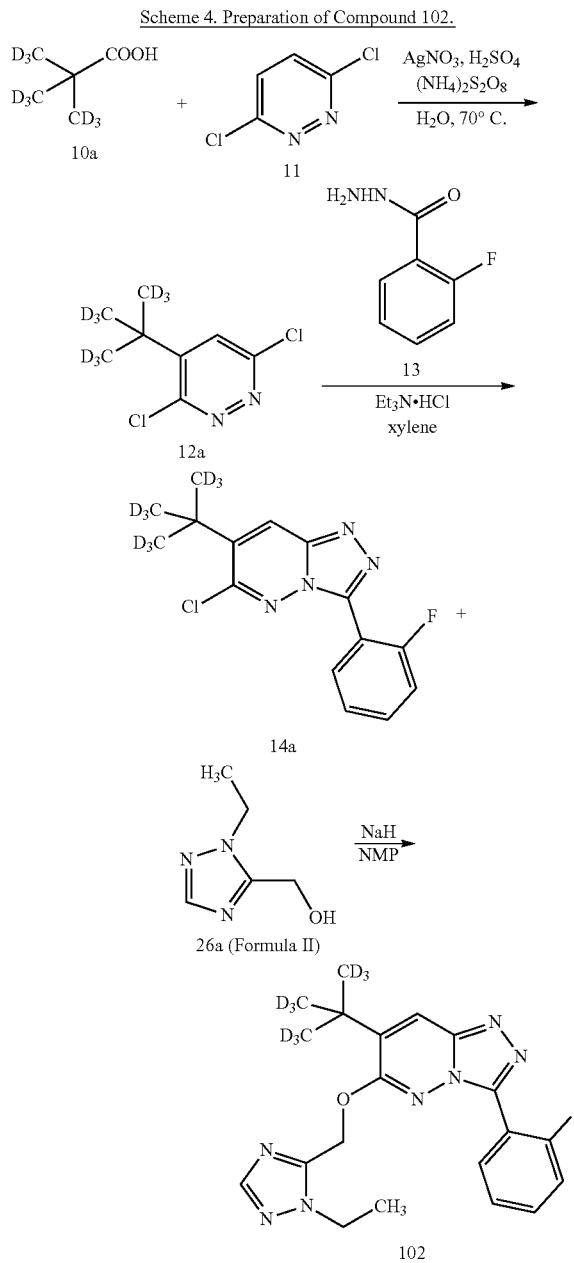

Step 1. 3,6-Dichloro-4-(1,1-dimethylethyl-$d_9$)pyridazine (12a)

Concentrated sulfuric acid (5.1 mL, 97 mmol) was added to a suspension of freshly purified 3,6-dichloro-pyridazine (11) (4.5 g, 30 mmol) in distilled water (125 mL). The mixture was warmed to 65° C. and trimethylacetic acid-$d_9$ (10a) (5.0 g, 454 mmol; CDN Isotopes, 98 atom % D) was added, followed by silver nitrate (1.0 g, 6 mmol). A solution of ammonium peroxydisulfate (10.2 g, 45 mmol) in distilled water (35 mL) was added over 10-15 min while keeping the reaction temperature at 65-75° C. The mixture was stirred for 30 min, then cooled to room temperature. The mixture was poured onto ice (100 g) and the solution adjusted to pH 9-10 with concentrated ammonium hydroxide. The aqueous mixture was extracted with dichloromethane (2×30 mL). The combined organic solution was washed with 1N NaOH (10 mL), dried over $Na_2SO_4$, filtered, and concentrated under reduced pressure. The crude product was purified by column chromatography an Analogix automated column chromatography system (40 g column, 0-15% EtOAc/heptane) to give 5.8 g (90%) of 12a as a colorless oil.

Note:
The use of freshly purified 3,6-dichloro-pyridazine is essential for achieving high yields in the foregoing reaction. 3,6-Dichloro-pyridazine (100 g) was purified by dissolving in EtOAc (500 mL) and washing with aqueous $NaHCO_3$ (2×50 mL) until all undissolved solids and yellow color were removed. The recovered material was then passed through a silica plug (250 g, 2:1 EtOAc/heptane) to give 95 g of white solid.

Step 2. 7-(tert-Butyl-$d_9$)-6-chloro-3-(2-fluorophenyl)-[1,2,4]triazolo[4,3-b]pyridazine (14a)

A mixture of 12a (5.8 g, 27.1 mmol), 13 (6.26 g, 40.6 mmol; prepared as described in Scheme 5 below), and triethylamine hydrochloride (5.6 g, 40.6 mmol) in xylene (60 mL) was heated at a gentle reflux with stirring for 3-4 days until TLC (2:1 EtOAc/heptane) showed the starting material was consumed. After cooling to room temperature the mixture was partially concentrated under reduced pressure. The residue was triturated with dichloromethane (40 mL) and filtered, and the filtrate was concentrated under reduced pressure. The crude product was purified by chromatography on an Analogix automated column chromatography system (SF25-80 g column, eluting with 10-60% EtOAc/heptane) to give 5.35 g (63%) of 14a as an off-white solid.

Step 3. 7-$d_9$-tert-Butyl-6-((1-ethyl-1H-1,2,4-triazol-5-yl)methoxy)-3-(2-fluorophenyl)-[1,2,4]-triazolo[4,3-b]pyridazine (102)

To a solution of 26a (400 mg, 3.14 mmol; prepared as described in Scheme 6 below) in NMP (10 mL) was added 60% sodium hydride in mineral oil (138 mg, 3.46 mmol). The thick, dark mixture was stirred for 15 min before 14a (890 mg, 2.86 mmol) was added. The mixture was stirred for 3 hr at room temperature then diluted with $H_2O$ (50 mL). The precipitate was collected by filtration and washed several times with water. The product was purified by recrystallization from EtOAc/heptane (1:1) then dried to give 778 mg (71%) of Compound 102 as an off-white solid. $^1$H-NMR (300 MHz, $CDCl_3$): δ 1.42 (t, J=7.2, 3H), 4.13 (q, J=7.2, 2H), 5.52 (s, 2H), 7.27 (app ddd, J=1.0, 8.3, 10.0, 1H), 7.35 (dt, J=1.2, 7.5, 1H), 7.52-7.60 (m, 1H), 7.87 (app dt, J=1.8, 7.2, 1H), 7.92 (s, 1H), 7.97 (s, 1H). $^{13}$C-NMR (75 MHz, $CDCl_3$): δ 15.21, 43.72, 59.02, 114.37, 114.56, 116.13, 116.41, 121.64, 124.51, 124.56, 131.67, 131.70, 132.25, 132.36, 137.65, 144.61, 144.90, 148.80, 151.21, 158.57, 158.67, 162.04. HPLC (method: Waters Atlantis T3 50 mm—gradient method 5-95% ACN+0.1% formic acid in 14 min with 4 min hold at 95% ACN+0.1% formic acid; wavelength: 305 nm): retention time: 5.78 min; 98.9% purity. MS (M+H): 405.3. Elemental Analysis ($C_{20}H_{13}D_9FN_7O$): Calculated: C=59.40, H=5.48, F=4.70, N=24.24. Found: C=59.24, H=5.47, F=4.64, N=24.01.

Example 2

Synthesis of 2-Fluorobenzohydrazide (13)

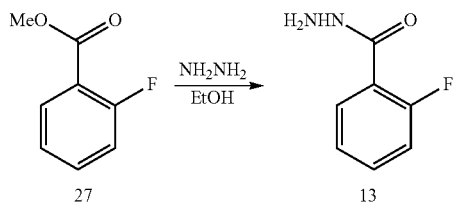

Scheme 5. Preparation of Intermediate 13.

2-Fluorobenzohydrazide (13)

Methyl 2-fluorobenzoate (27) (25 g, 160 mmol) was dissolved in ethanol (200 mL) and hydrazine monohydrate (11.8 mL, 240 mmol) was added. The mixture was heated to reflux for 4 hr then allowed to cool to room temperature overnight. The reaction was incomplete. After heating for a further 2 hr, starting material still remained. Additional hydrazine monohydrate (4 mL) was added. After heating for 2-3 hr the reaction was nearly complete. The mixture was cooled and concentrated under reduced pressure. Water (50 mL) was added to the residue and the aqueous layer was saturated with solid NaCl. The product was extracted with EtOAc (3×100 mL). The combined organic solution was dried over $Na_2SO_4$, filtered, and concentrated under reduced pressure. The residue was triturated with heptane (100 mL), filtered, and dried to provide 23.8 g (95%) of 13 as a pinkish solid.

Example 3

Synthesis of 1-Ethyl-1H-1,2,4-triazole (26a)

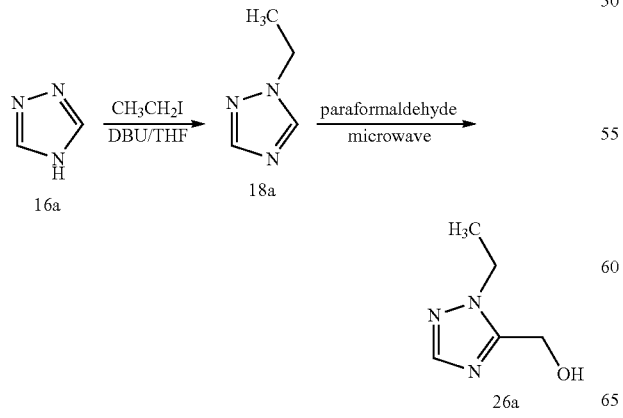

Scheme 6. Preparation of Intermediate 26a.

Step 1. 1-Ethyl-1H-1,2,4-triazole (18a)

To an ice-cold solution of 1,2,4-triazole (5 g, 72.4 mmol) in anhydrous THF (50 mL) was added ethyl iodide (7 mL, 86.9 mmol). DBU (10.8 mL, 72.4 mmol) was added dropwise to the cloudy system over 10-20 min. The reaction was allowed to slowly warm to room temperature and was stirred overnight. The mixture was filtered through a Celite pad and the filtrate was concentrated under reduced pressure to give 10 g of crude material as a yellow liquid. The crude material was Kugelrohr-distilled (at approximately 300 mtorr, 35-40° C.) to provide 4.9 g (70%) of 18a as clear liquid.

Step 2. (1-Ethyl-1H-1,2,4-triazol-5-yl)methanol (26a)

A mixture of 18a (0.5 g, 5.1 mmol) and paraformaldehyde (0.8 g) were heated at 170° C. for 2 hr under microwave irradiation in a 10-mL tube. The mixture was cooled to room temperature and diluted with dichloromethane (10 mL). The solid was removed by filtration and the filtrate was concentrated under reduced pressure. Two runs (total of 10.3 mmol) were combined and the crude product was purified on an Analogix automated column chromatography system (24 g column, 0-4% MeOH/dichloromethane) to give 410 mg of 26a as a white solid.

Example 4

Synthesis of (1-$d_5$-Ethyl-1H-1,2,4-triazol-5-yl)methanol (26b)

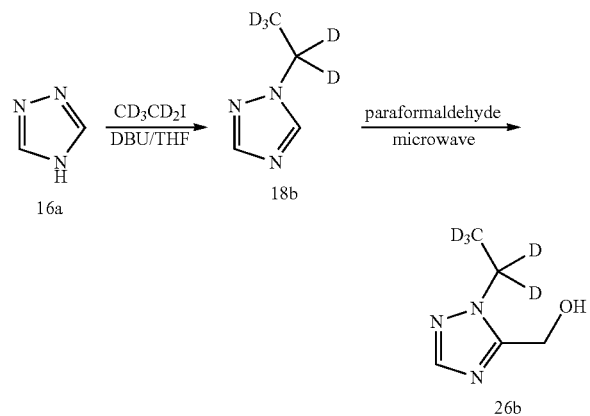

Scheme 7. Preparation of Intermediate 26b.

Step 1. 1-Ethyl-$d_5$-1H-1,2,4-triazole (18b):

The compound was prepared as described for 18a above, but using iodoethane-$d_5$ (Aldrich, 99.5 atom % D).

Step 2. (1-$d_5$-Ethyl-1H-1,2,4-triazol-5-yl)methanol (26b)

The compound was prepared as described for 26a above, but using 18b.

Example 5

Synthesis of (1-d₅-Ethyl-1H-1,2,4-triazol-5-yl)methan-d₂-ol (Compound 302)

Scheme 8. Preparation of Compound 302.

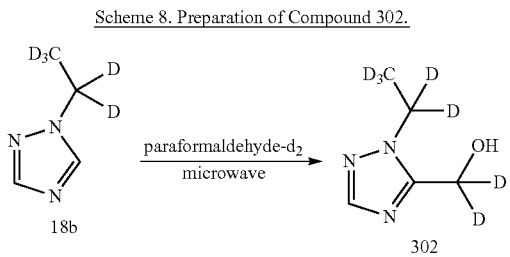

(1-d₅-Ethyl-1H-1,2,4-triazol-5-yl)methan-d₂-ol (Compound 302)

The compound was prepared as described for 26a above, but using 18b. ¹H-NMR (300 MHz, CDCl₃): δ 5.81 (s, 1H), 7.77 (s, 1H). ¹³C-NMR (75 MHz, CDCl₃): δ 149.64, 153.85. HPLC (method: Waters Atlantis T3 2.1×50 mm—gradient method 5-95% ACN+0.1% formic acid in 14 min with 4 min hold at 95% ACN+0.1% formic acid; wavelength: 305 nm): retention time: 0.246 min.>95% purity (NMR). MS (M+H): 135.0.

Example 6

Synthesis of 7-d₉-tert-Butyl-6-((1-d₅-ethyl-1H-1,2,4-triazol-5-yl)-methoxy-d₂)-3-(2-fluorophenyl)-[1,2,4]triazolo[4,3-b]pyridazine (Compound 106)

Scheme 9. Preparation of Compound 106.

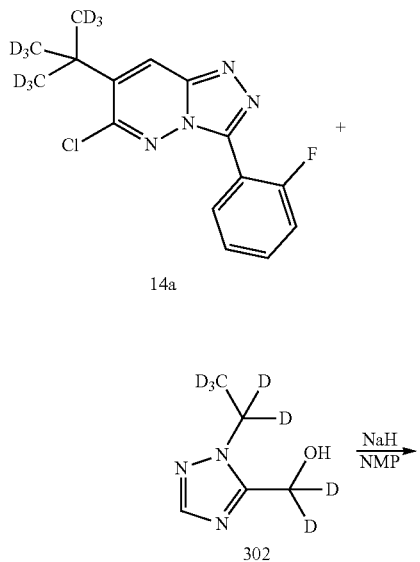

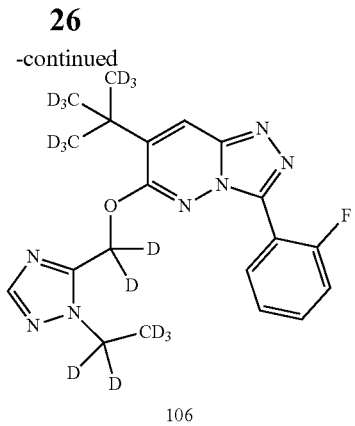

7-d₉-tert-Butyl-6-(1-d₅-ethyl-1H-1,2,4-triazol-5-yl)methoxy-d₂)-3-(2-fluorophenyl)-[1,2,4]triazolo[4,3-b]pyridazine (Compound 106)

To a solution of 302 (300 mg, 2.24 mmol; prepared as described in Scheme 6) in NMP (8 mL) was added 60% sodium hydride in mineral oil (98 mg, 2.46 mmol). The thick, dark mixture was stirred for 15 min before 14a (638 mg, 2.03 mmol; prepared as described in Scheme 4) was added. The mixture was stirred for 3 hr at room temperature, then diluted first with D₂O (5 mL), then H₂O (40 mL). The precipitate was collected by filtration and washed several times with water. The product was purified by recrystallization from EtOAc/heptane (1:1) then dried to give 607 mg (73%) of 106 as a white solid. ¹H-NMR (300 MHz, CDCl₃): δ 7.27 (app dddd, J=0.4, 1.2, 8.3, 10.4, 1H), 7.35 (dt, J=1.2, 7.5, 1H), 7.52-7.60 (m, 1H), 7.87 (app ddt, J=0.3, 1.8, 6.2, 1H), 7.92 (s, 1H), 7.97 (s, 1H). ¹³C-NMR (75 MHz, CDCl₃): δ 114.42, 114.61, 116.15, 116.42, 121.67, 124.53, 124.57, 131.70, 131.74, 132.27, 132.38, 137.65, 144.60, 144.93, 148.76, 151.26, 158.59, 158.69, 162.06. HPLC (method: Waters Atlantis T3 50 mm—gradient method 5-95% ACN+0.1% formic acid in 14 min with 4 min hold at 95% ACN+0.1% formic acid; wavelength: 305 nm): retention time: 5.73 min; 99.1% purity. MS (M±H): 412.2. Elemental Analysis (C₂₀H₆D₁₆FN₇O): Calculated: C=58.38, H=5.39, F=4.62, N=23.83. Found: C=58.21, H=5.37, F=4.61, N=23.82.

Example 7

Synthesis of 7-d₉-tert-Butyl-6-(1-d₅-ethyl-1H-1,2,4-triazol-5-yl)methoxy)-3-(2-fluorophenyl)-[1,2,4]triazolo[4,3-b]pyridazine (Compound 105)

Scheme 10. Preparation of Compound 105.

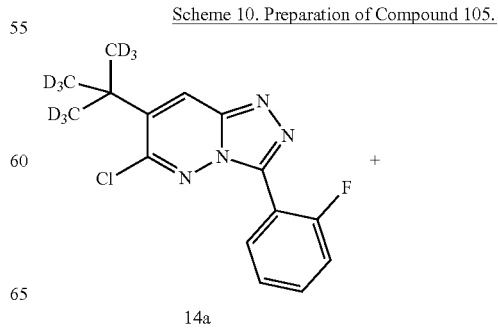

-continued

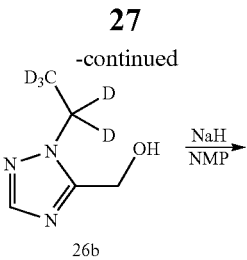

26b

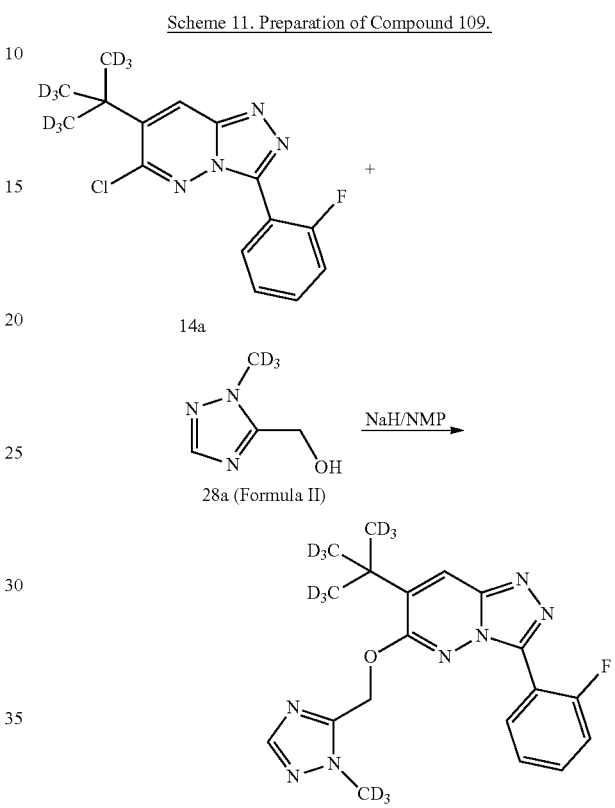

105

7-d₉-tert-Butyl-6-((1-d₅-ethyl-1H-1,2,4-triazol-5-yl)methoxy)-3-(2-fluorophenyl)-[1,2,4]triazolo[4,3-b]pyridazine (105)

To a solution of 26b (278 mg, 2.1 mmol; prepared as described in Scheme 7) in NMP (4 mL) was added 60% sodium hydride in mineral oil (93 mg, 2.3 mmol). The thick, dark mixture was stirred for 15 min before 14a (600 mg, 1.9 mmol; prepared as described in Scheme 4) was added. The mixture was stirred for 1-2 hr at room temperature then diluted with water (40 mL). The precipitate was collected by filtration and washed several times with water. The crude product was purified by column chromatography on an Analogix automated column chromatography system (12 g column, eluting with 0-100% EtOAc/heptane) to give 530 mg (68%) of 105 as a white solid. $^1$H-NMR (300 MHz, CDCl$_3$): δ 5.50 (s, 2H), 7.27 (app dd, J=1.0, 8.2, 10.2, 1H), 7.34 (dt, J=1.0, 7.6, 1H), 7.51-7.60 (m, 1H), 7.86 (app dt, J=1.8, 7.3, 1H), 7.92 (s, 1H), 7.96 (s, 1H). $^{13}$C-NMR (75 MHz, CDCl$_3$): δ 59.02, 114.38, 114.57, 116.11, 116.40, 121.64, 124.49, 124.54, 131.66, 131.70, 132.23, 132.34, 137.61, 144.60, 144.90, 148.79, 151.22, 158.55, 158.65, 162.03. HPLC (method: Waters Atlantis T3 2.1 column 2.1×50 mm—gradient method 5-95% ACN 0.1% formic acid in 14 min with 4 min hold at 95% ACN+0.1% formic acid; wavelength: 305 nm): retention time: 5.73 min; 98.4% purity. MS (M+H): 410.1. Elemental Analysis (C$_{20}$H$_8$D$_{14}$FN$_7$O): Calculated: C=58.67, H=5.42, F=4.64, N=23.95.

Found: C=58.69, H=5.24, F=4.64, N=24.05.

Example 8

Synthesis of 7-d₉-tert-Butyl-3-(2-fluorophenyl)-6-((1-d₃-methyl-1H-1,2,4-triazol-5-yl)methoxy)-[1,2,4]triazolo[4,3-b]pyridazine (Compound 109)

Scheme 11. Preparation of Compound 109.

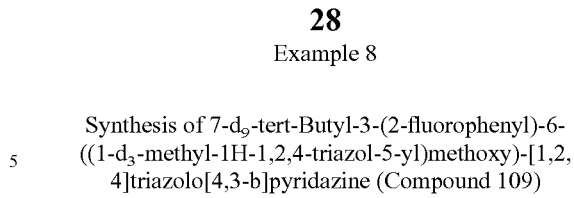

7-d₉-tert-Butyl-3-(2-fluorophenyl)-6-((1-d₃-methyl-1H-1,2,4-triazol-5-yl)methoxy)-[1,2,4]triazolo[4,3-b]pyridazine (109)

To a solution of 28a (400 mg, 3.44 mmol; prepared as described in Scheme 12) in NMP (10 mL) was added 60% sodium hydride in mineral oil (151 mg, 3.79 mmol). The thick, dark mixture was stirred for 15 min before 14a (980 mg, 3.13 mmol; prepared as described in Scheme 4) was added. The mixture was stirred for 3 hr at room temperature then diluted with water (50 mL). The precipitate was collected by filtration and washed several times with water. The crude product was purified by recrystallization from EtOAc/heptane (1:1) then dried to give 948 mg (77%) of 109 as a white solid. $^1$H-NMR (300 MHz, CDCl$_3$): δ 5.51 (s, 2H), 7.27 (app ddd, J=0.7, 8.3, 10.2, 1H), 7.35 (dt, J=1.1, 7.6, 1H), 7.51-7.60 (m, 1H), 7.85 (app dt, J=1.9, 7.2, 1H), 7.90 (s, 1H), 7.97 (s, 1H). $^{13}$C-NMR (75 MHz, CDCl$_3$): δ 60.34, 115.54, 117.32, 117.60, 122.86, 125.71, 125.76, 132.87, 132.90, 133.48, 133.59, 138.81, 145.75, 146.08, 150.82, 152.30, 159.73, 159.87, 163.23. HPLC (method: Waters Atlantis T3 50 mm—gradient method 5-95% ACN+0.1% formic acid in 14 min with 4 min hold at 95% ACN+0.1% formic acid; wavelength: 305 nm): retention time: 5.18 min; 99.2% purity. MS (M+H): 394.2. Elemental Analysis ($C_{19}H_8D_{12}FN_7O.0.2H_2O$): Calculated: C=57.48, H=5.23, F=4.79, N=24.70. Found: C=57.25, H=5.23, F=4.66, N=24.48.

Example 9

Synthesis of (1-Methyl-$d_3$-1H-1,2,4-triazol-5-yl)methanol (28a)

Scheme 12. Preparation of Intermediate 28a.

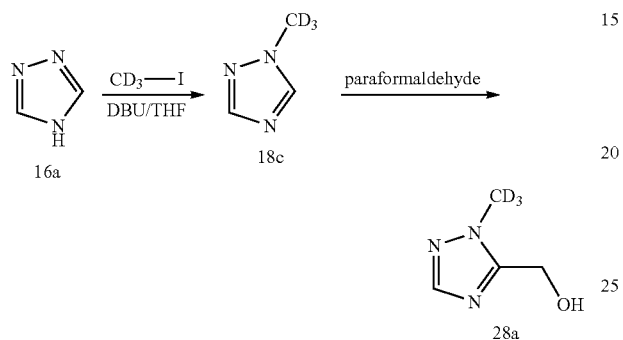

Step 1. 1-Methyl-$d_3$-1H-1,2,4-triazole (18c)

To an ice-cold solution of 1,2,4-triazole (6.0 g, 87 mmol) in anhydrous THF (60 mL) was added iodomethane-$d_3$ (6.5 mL, 1.05 mol; Cambridge Isotopes, 99.5 atom % D). To the cloudy system was added DBU (13.2 mL, 87 mmol) over 20-30 min. The reaction was allowed to slowly warm to room temperature and was stirred overnight. The mixture was filtered through a Celite pad, and the filtrate was concentrated under reduced pressure to give 5.3 g of crude product as yellow oil. The sample was Kugelrohr-distilled (approximately 350 mtorr, 25-30° C.) to give 2.67 g of 18c as clear liquid.

Step 2. (1-Methyl-$d_3$-1H-1,2,4-triazol-5-yl)methanol (28a)

A mixture of 18c (5 g, 58 mmol) and paraformaldehyde (10 g, 333 mmol) were heated in a sealed tube at 170° C. for 5 hr. The mixture was cooled to room temperature and diluted with dichloromethane (20 mL). The solid was removed by filtration and the filtrate was concentrated under reduced pressure. The crude product was purified by chromatography on a short column of silica gel, eluting with 5% methanol/dichloromethane to give 5.0 g (75%) of 28a as an off-white solid.

Example 10

Synthesis of (1-$d_3$-Methyl-1H-1,2,4-triazol-5-yl)methan-$d_2$-ol (Compound 301)

Scheme 13. Preparation of Compound 301.

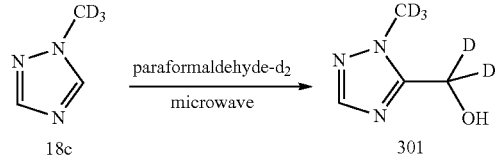

(1-Methyl-$d_3$-1H-1,2,4-triazol-5-yl)methan-$d_2$-ol (301)

A mixture of 18c (0.5 g, 5.8 mmol) and paraformaldehyde-$d_2$ (0.9 g; Cambridge Isotopes, 99 atom % D) were heated at 170° C. for 2 hr under microwave irradiation (10 mL tube). The mixture was cooled to room temperature and diluted with dichloromethane (10 mL). The solid was removed by filtration and the filtrate was concentrated under reduced pressure. Five runs (total 29 mmol) were combined and the crude product was purified on an Analogix automated column chromatography system (24 g column, 0-5% MeOH/dichloromethane) to give 1.2 g of clean 301 as a white solid plus 1.68 g of less pure material as an oil. $^1$H-NMR (300 MHz, CDCl$_3$): δ 5.62 (s, 1H), 7.76 (s, 1H). $^{13}$C-NMR (75 MHz, CDCl$_3$): δ 149.65, 154.50. HPLC (method: Waters Atlantis T3 2.1×50 mm—gradient method 5-95% ACN+0.1% formic acid in 14 min with 4 min hold at 95% ACN+0.1% formic acid; wavelength: 305 nm): retention time: 0.24 min.>95% purity (NMR). MS (M+H): 119.1.

Example 11

Synthesis 7-$d_9$-tert-Butyl-3-(2-fluorophenyl)-6-((1-$d_3$-methyl-1H-1,2,4-triazol-5-yl)-methoxy-$d_2$)-[1,2,4]triazolo[4,3-b]pyridazine (Compound 110)

Scheme 14. Preparation of Compound 110.

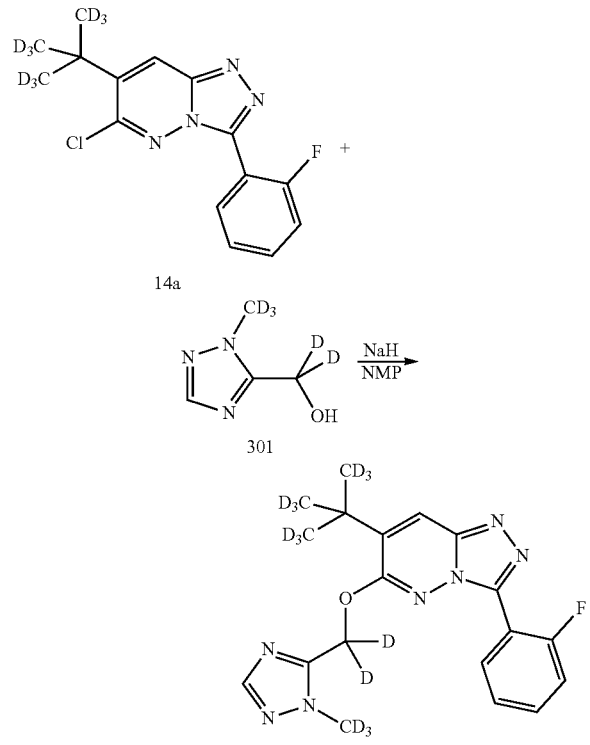

7-$d_9$-tert-Butyl-3-(2-fluorophenyl)-6-((1-$d_3$-methyl-1H-1,2,4-triazol-5-yl)-methoxy-$d_2$)-[1,2,4]-triazolo[4,3-b]pyridazine (Compound 110)

To a solution of compound 301 (250 mg, 2.12 mmol; prepared as described in Scheme 13) in NMP (5 mL) was added 60% sodium hydride in mineral oil (93 mg, 2.33 mmol). The thick, dark mixture was stirred for 15 min before 14a (603 mg, 1.92 mmol) was added. The mixture was stirred for 1-2 hr at room temperature then diluted with water (50 mL). The precipitate was collected by filtration and washed several times with water. The crude product was purified by recrystallization from EtOAc/heptane (1:1) then dried to give 560 mg (74%) of 110 as a white solid. $^1$H-NMR (300 MHz, CDCl$_3$): δ 7.27 (app dddd, J=0.3, 1.2, 8.3, 10.1, 1H), 7.35 (dt, J=1.1, 7.6, 1H), 7.52-7.60 (m, 1H), 7.85 (app ddt, J=0.3, 1.8, 7.2, 1H), 7.90 (s, 1H), 7.97 (s, 1H). $^{13}$C-NMR (75 MHz, CDCl$_3$): δ 114.36, 114.55, 116.12, 116.41, 121.67, 124.51, 124.56, 131.68, 131.72, 132.28, 132.39, 137.62, 144.89, 151.13, 158.54, 158.68, 162.04. HPLC (method: Waters Atlantis T3 50 mm—gradient method 5-95% ACN+0.1% formic acid in 14 min with 4 min hold at 95% ACN+0.1% formic acid; wavelength: 305 nm): retention time: 5.12 min; 98.7% purity. MS (M+H): 396.3. Elemental Analysis (C$_{19}$H$_6$D$_{14}$FN$_7$O): Calculated: C=57.71, H=5.10, F=4.80, N=24.80. Found: C=57.57, H=5.02, F=4.81, N=24.87.

Example 12

Synthesis of 2-(6-(((1-ethyl-1H-1,2,4-triazol-5-yl) methoxy)-3-(2-fluorophenyl)[1,2,4]triazolo[4,3-b] pyridazin-7-yl)propan-1,1,1,3,3,3-d$_6$-2-ol (Compound 202)

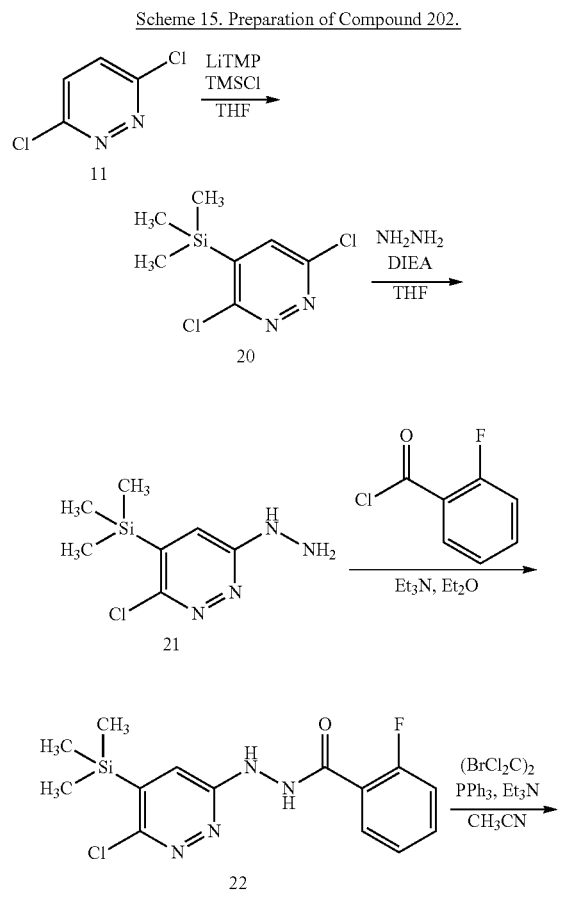

Scheme 15. Preparation of Compound 202.

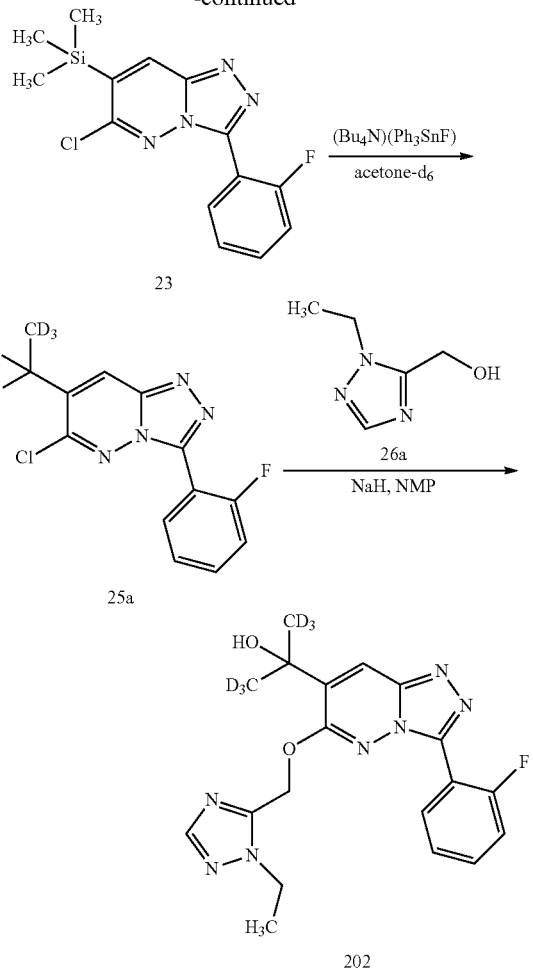

Step 1. 3,6-Dichloro-4-(trimethylsilyl)pyridazine (20)

A four-neck flask equipped with a mechanical stirrer, thermowell, and addition funnel was charged with 2,2,6,6-tetramethylpiperidine (25.1 mL, 147.7 mmol) and anhydrous THF (200 mL). The solution was cooled to −10° C.-0° C. and n-BuLi (2.5 M in hexanes, 59 mL, 147.7 mmol) was added over 10 min. The solution was stirred for 15-20 min then further cooled to −78° C. A mixture of freshly purified 3,6-dichloro-pyridazine (10 g, 67.1 mmol) and trimethylsilyl chloride (9.3 mL, 73.8 mmol) in THF (100 mL) was added dropwise via an addition funnel. The dark red solution was stirred at −78° C. for 1 hr, at which point the reaction was complete. The reaction was quenched cold with saturated ammonium chloride solution (100 mL) and immediately diluted with MTBE (200 mL). The layers were separated while still cold (additional water was added if necessary until all solids dissolved) and the aqueous phase was washed with MTBE (100 mL). The combined organic solution was washed with dilute citric acid solution (30 mL portions) until the aqueous washes were pH 6-7. The organic solution was then washed with brine, dried over Na$_2$SO$_4$, and concentrated to a residue. The crude material was purified by column chromatography on silica gel (100 g, 2:1 heptane:EtOAc) to provide 13.6 g of 20 as a reddish oil.

Note:

Immediate purification is required for best yields. The crude and purified materials degraded upon prolonged storage at 5° C.

Step 2.
3-Chloro-6-hydrazinyl-4-(trimethylsilyl)pyridazine (21)

A round-bottom flask under $N_2$ was charged with 20 (13.6 g, 61.4 mmol) and anhydrous hydrazine (1M in THF, 184 mL, 184 mmol) followed by diisopropylethyl amine (11 mL, 61.4 mmol). The reaction was heated to a gentle reflux (70-75° C., external temperature) monitoring the reaction by LCMS. After 4 days the dark mixture was cooled, silica gel (20 g) was added and the mixture was concentrated. The crude mixture was combined with the crude material from a second reaction (16 mmol) and purified on a silica column (120 g, 0-5% MeOH/dichloromethane) to provide 7.5 g (45%) of 21 as a reddish oil/solid mix. Some trace impurities and residual diisopropylethyl amine remained. The product was used 'as is' in the next step.

Step 3. N'-(6-Chloro-5-(trimethylsilyl)pyridazin-3-yl)-2-fluorobenzohydrazide (22)

A solution of 21 (6.45 g, 30 mmol) and triethylamine (5 mL, 36 mmol) in diethyl ether (120 mL) was cooled to 0-5° C. in an ice bath. 2-Fluorobenzoyl chloride (4.8 g, 30 mmol) was added dropwise keeping the temperature less than 5° C. The reaction was stirred 30 min then quenched by the addition of anhydrous MeOH (0.4 mL). The mixture was diluted with hexane (100 mL) and filtered. The solids were washed with ether (2×15 mL), then water (30 mL). The solids were dissolved in dichloromethane (100 mL) with a small amount of MeOH to aid solubility, then washed with brine. The organic solution was dried over $Na_2SO_4$ and concentrated to give a 51.7% yield of 22 as a brownish solid.

Step 4. 6-Chloro-3-(2-fluorophenyl)-7-(trimethylsilyl)-[1,2,4]triazolo[4,3-b]pyridazine (23)

Compound 22 (4.1 g, 12.1 mmol) and 1,2-dibromotetrachloroethane (7.9 g, 24.2 mmol) were suspended in acetonitrile (80 mL) and cooled to less than 5° C. Triphenylphosphine (11 g, 30.2 mmol) was added in small portions allowing the reaction to exotherm slightly but keeping the temperature at about 5-7° C. The solids started to dissolve and then a new precipitate began to form. The thick mixture was stirred cold for 15 min. Triethylamine (10 mL, 72.6 mmol) was added dropwise, again allowing an exotherm but keeping the temperature about 5-7° C. The reaction was stirred in an ice-water bath for 1 hr. The mixture was diluted with dichloromethane (200 mL) and washed with water. The organic layer was dried over $Na_2SO_4$ and concentrated to a brown liquid. The material was combined with crude material from another (2.9 mmol) reaction and purified on an Analogix automated column chromatography system (SF25-80 g column, 10-40% EtOAc/heptane) to provide 3.8 g (79%) of 23 as a tan, slightly sticky, solid.

Step 5. 2-(6-Chloro-3-(2-fluorophenyl)-[1,2,4]triazolo[4,3-b]pyridazin-7-yl) propan-1,1,1,3,3,3-$d_6$-2-ol (25a)

Tetrabutylammonium difluorotriphenylstannate (400 mg) was added in one portion to a solution of 23 (500 mg, 1.56 mmol) in acetone-$d_6$ (5 mL; Aldrich 99.9 atom % D) at room temperature. The reaction was stirred for 1 hr. Five runs (total 7.8 mmol) were combined and concentrated under reduced pressure. The crude material was purified by column chromatography on an Analogix automated column chromatography system (60 g column, 0-5% MeOH/dichloromethane) to provide 1.24 g (43%) of 25a as amorphous foam. LCMS showed the material to be approximately 90% purity.

Step 6. 2-(6-((1-Ethyl-1H-1,2,4-triazol-5-yl)methoxy)-3-(2-fluorophenyl)-[1,2,4]triazolo[4,3-b]pyridazin-7-yl)propan-1,1,1,3,3,3-$d_6$-2-ol (Compound 202)

To a solution of 26a (134 mg, 1.06 mmol; prepared as described in Scheme 6) in NMP (2 mL) was added portionwise 60% sodium hydride in mineral oil (46 mg, 1.15 mmol). The thick, dark mixture was stirred for 15 min before 25a (300 mg, 0.96 mmol) was added. The mixture was stirred for 2 hr at room temperature then diluted with water (20 mL). The mixture was extracted with EtOAc (3×20 mL). The aqueous layer was neutralized with dilute citric acid solution and extracted with EtOAc (2×20 mL) to recover some residual product. The combined organic solution was dried over $Na_2SO_4$ and concentrated. The crude product was combined with the crude product from another (0.64 mmol) reaction and purified by chromatography on an Analogix automated column chromatography system (24 g column, 0-5% MeOH/dichloromethane) to provide 780 mg of compound 202 as a brownish solid. The material was triturated with heptane to remove some a residual NMP and 560 mg of material was recovered. The product was then recrystallized from EtOAc/heptane to give 226 mg of 202 as a light tan solid. The filtrates were re-processed to recover another 20 mg of material. $^1$H-NMR (300 MHz, CDCl$_3$): δ 1.38 (t, J=7.7, 3H), 3.53 (s, 1H), 4.10 (q, J=7.7, 2H), 5.53 (s, 2H), 7.27 (app ddd, J=1.0, 8.3, 10.0, 1H), 7.34 (dt, =1.1, 7.8, 1H), 7.51-7.60 (m, 1H), 7.83 (app dt, J=1.8, 7.2, 1H), 7.89 (s, 1H), 8.31 (s, 1H). $^{13}$C-NMR (75 MHz, CDCl$_3$): δ 15.21, 43.74, 59.35, 70.94, 114.25, 114.44, 116.11, 116.39, 121.88, 124.57, 124.62, 131.78, 131.81, 132.39, 132.50, 135.82, 144.75, 144.85, 144.83, 148.67, 151.22, 157.43, 158.66, 162.03. HPLC (method: Waters Atlantis T3 2.1 column 2.1×50 mm—gradient method 5-95% ACN+0.1% formic acid in 14 min with 4 min hold at 95% ACN+0.1% formic acid; wavelength: 305 nm): retention time: 4.27 min; 98.0% purity. MS (M+H): 404.4. Elemental Analysis ($C_{19}H_{14}D_6FN_7O_2$): Calculated: C=56.57, H=5.00, F=4.71, N=24.30. Found: C=56.60, H=4.59, F=4.61, N=23.57.

Example 13

Synthesis of 2-(6-((1-$d_5$-Ethyl-1H-1,2,4-triazol-5-yl)methoxy-$d_2$)-3-(2-fluorophenyl)-[1,2,4]triazolo[4,3-b]pyridazin-7-yl)propan-1,1,1,3,3,3-$d_6$-2-ol (Compound 206)

Scheme 16. Preparation of Compound 206.

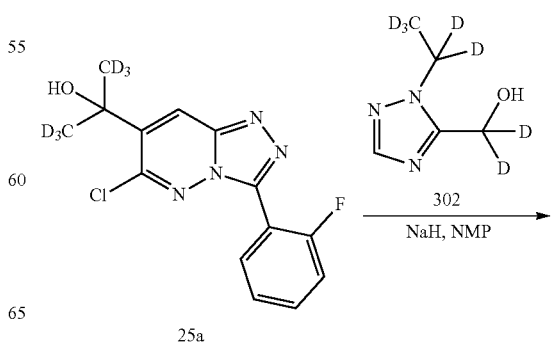

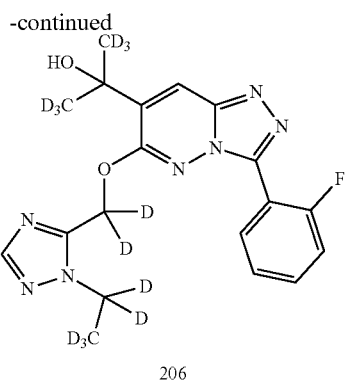

206

2-(6-((1-$d_5$-Ethyl-1H-1,2,4-triazol-5-yl)methoxy-$d_2$)-3-(2-fluorophenyl)-[1,2,4]triazolo[4,3-b]pyridazin-7-yl)propan-1,1,1,3,3,3-$d_6$-2-ol (206)

To a solution of compound 302 (236 mg, 1.76 mmol; prepared as described in Scheme 8) in NMP (2 mL) was added portion-wise 60% sodium hydride in mineral oil (77 mg, 1.92 mmol). The thick, dark mixture was stirred for 15 min before 25a (500 mg, 1.6 mmol) was added. The mixture was stirred for 2 hr at room temperature then diluted with water (20 mL). The product was extracted with EtOAc (3×30 mL). The aqueous layer was neutralized with dilute citric acid solution and extracted with EtOAc (2×20 mL) to recover some residual product. The combined organic solution was dried over $Na_2SO_4$ and concentrated. The crude product was purified by chromatography on an Analogix automated column chromatography system (24 g column, 0-5% MeOH/dichloromethane to provide 850 mg of 206 as a tan solid. The material was triturated with heptane to remove some residual NMP. The product was then recrystallized from EtOAc/heptane to give 290 mg of 206 as a light tan solid. The filtrates were re-processed to recover another 40 mg of material. $^1$H-NMR (300 MHz, $CDCl_3$): δ 3.38 (s, 1H), 4.10 (q, J=7.7, 2H), 5.53 (s, 2H), 7.27 (app ddd, J=1.0, 8.3, 10.5, 1H), 7.35 (dt, J=1.2, 7.4, 1H), 7.53-7.61 (m, 1H), 7.85 (app dt, J=1.8, 7.2, 1H), 7.90 (s, 1H), 8.31 (s, 1H). $^{13}$C-NMR (75 MHz, $CDCl_3$): δ 114.29, 114.48, 116.12, 116.40, 121.91, 124.60, 124.65, 131.81, 131.85, 132.41, 132.52, 135.71, 144.77, 151.27, 157.44, 158.68, 162.05. HPLC (method: Waters Atlantis T3 2.1 column 2.1×50 mm—gradient method 5-95% ACN+0.1% formic acid in 14 min with 4 min hold at 95% ACN+0.1% formic acid; wavelength: 305 nm): retention time: 4.24 min; 98.0% purity. MS (M+H): 411.3. Elemental Analysis ($C_{19}H_7D_{13}FN_7O_2$): Calculated: C=55.60, H=4.91, F=4.63, N=23.89. Found: C=55.43, H=4.81, F=4.63, N=23.31.

Example 14

Evaluation of Metabolic Stability in Human Liver Microsomes

Microsomal Assay:

Human liver microsomes (20 mg/mL) were obtained from Xenotech, LLC (Lenexa, Kans.). β-nicotinamide adenine dinucleotide phosphate, reduced form (NADPH), magnesium chloride ($MgCl_2$), and dimethyl sulfoxide (DMSO) were purchased from Sigma-Aldrich.

Determination of Metabolic Stability:

7.5 mM stock solutions of test compounds were prepared in DMSO. The 7.5 mM stock solutions were diluted to 12.5 μM in acetonitrile (ACN). The 20 mg/mL human liver microsomes were diluted to 2.5 mg/mL in 0.1 M potassium phosphate buffer, pH 7.4, containing 3 mM $MgCl_2$. The diluted microsomes were added to wells of a 96-well deep-well polypropylene plate in triplicate. A 10 μL aliquot of the 12.5 μM test compound was added to the microsomes and the mixture was pre-warmed for 10 minutes. Reactions were initiated by addition of pre-warmed NADPH solution. The final reaction volume was 0.5 mL and contains 2.0 mg/mL human liver microsomes, 0.25 μM test compound, and 2 mM NADPH in 0.1 M potassium phosphate buffer, pH 7.4, and 3 mM $MgCl_2$. The reaction mixtures were incubated at 37° C., and 50 μL aliquots were removed at 0, 5, 10, 20, and 30 minutes and added to shallow-well 96-well plates which contain 50 μL of ice-cold ACN with internal standard to stop the reactions. The plates were stored at 4° C. for 20 minutes after which 100 μL of water was added to the wells of the plate before centrifugation to pellet precipitated proteins. Supernatants were transferred to another 96-well plate and analyzed for amounts of parent remaining by LC-MS/MS using an Applied Bio-systems API 4000 mass spectrometer. The same procedure was followed for TPA-023 and the positive control, 7-ethoxycoumarin (1 μM). Testing was done in triplicate and individual compounds were tested in two or four different runs.

The in vitro $t_{1/2}$s for test compounds were calculated from the slopes of the linear regression of % parent remaining (ln) vs incubation time relationship:

in vitro $t_{1/2}$=0.693/k k=−[slope of linear regression of % parent remaining (ln)vs incubation time].

Data analysis was performed using Microsoft Excel Software.

Figure 2:
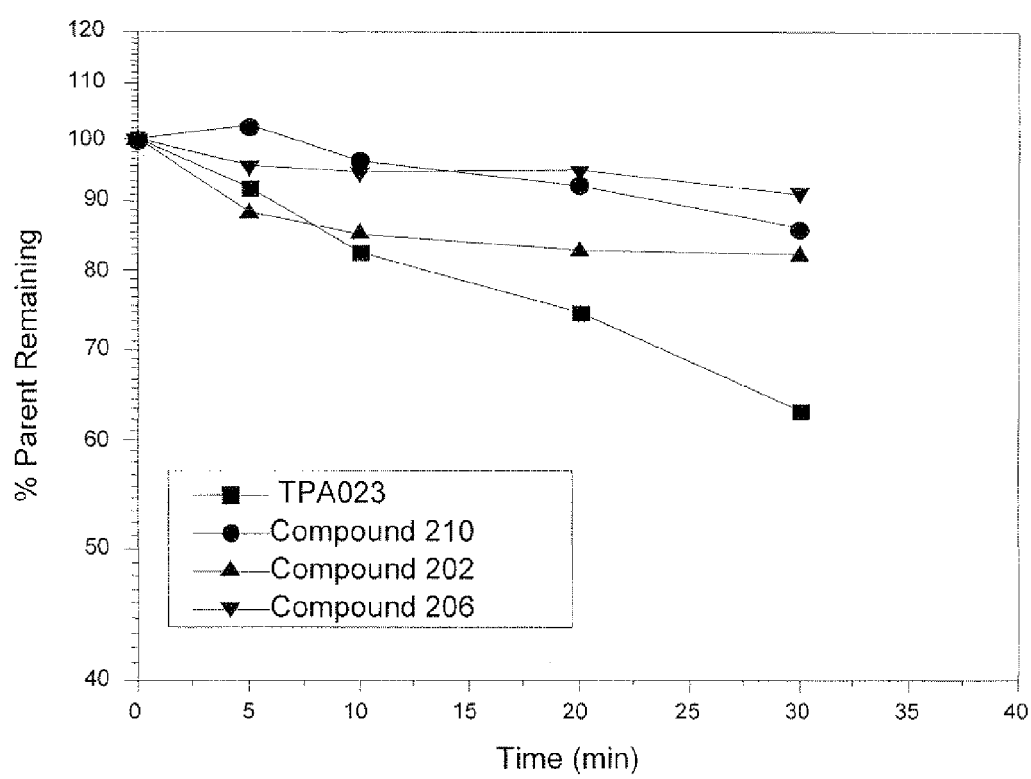
FIG. 2 depicts the time course of disappearance of certain other compounds of the invention during incubation with human liver microsomes.

The results of these experiments are shown in Table 3, below, and in FIGS. 1 and 2. In the Table and the two Figures, "% Parent remaining" refers to the percentage of starting material remaining at the specified time point.

TABLE 3

Stability of Compounds of the Invention in Human Liver Microsomes.

| Compound ID Expt # | % Parent Remaining (30 min) Ave ± SD | $t_{1/2}$ (min) Ave ± SD |
|---|---|---|
| TPA023 | 62 ± 3.1 | 44.5 ± 4.4 |
| Compound 102 | 80 ± 3.3 | 85.6 ± 6.1 |
| Compound 105 | 90 ± 0.7 | NC* |
| Compound 106 | 89 ± 2.5 | NC* |
| Compound 109 | 100 ± 5.7 | NC* |
| Compound 110 | 91 ± 7.1 | NC* |
| Compound 210 | 86 ± 4.2 | NC* |
| Compound 202 | 82 ± 2.8 | NC* |
| Compound 206 | 92 ± 3.5 | NC* |

*$t_{1/2}$ not calculable due to <20% metabolism in HLM and flat % parent remaining vs time profiles Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:

1. A compound of Formula I:

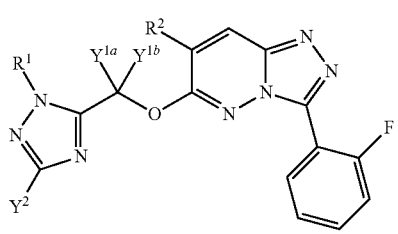

(I)

or a pharmaceutically acceptable salt thereof, wherein:
  $R^1$ is —CH$_3$, or —CH$_2$CH$_3$, wherein $R^1$ is optionally substituted with deuterium;
  $R^2$ is —CZ(R$^3$)$_2$;
  Z is —OH or —CH$_3$, wherein the —CH$_3$ of Z is optionally substituted with deuterium;
  each $R^3$ is —CH$_3$ wherein each $R^3$ is optionally substituted with deuterium;
  each $Y^1$ is independently hydrogen or deuterium; and
  $Y^2$ is hydrogen or deuterium;
  with the proviso that when $R^1$ is unsubstituted —CH$_3$ or unsubstituted —CH$_2$CH$_3$ Z is unsubstituted —CH$_3$; and $R^2$ is not substituted with deuterium; then at least one of $Y^1$ and $Y^2$ is deuterium.

2. The compound of claim 1, wherein $R^1$ is —CH$_3$, —CD$_3$, —CH$_2$CH$_3$, CD$_2$CH$_3$, —CH$_2$CD$_3$, or —CD$_2$CD$_3$.

3. The compound of claim 2, wherein $R^1$ is —CH$_2$CH$_3$, —CD$_2$CH$_3$, —CH$_2$CD$_3$, or —CD$_2$CD$_3$.

4. The compound of claim 1, wherein $Y^{1a}$ and $Y^{1b}$ are hydrogen.

5. The compound of claim 1, wherein $Y^{1a}$ and $Y^{1b}$ are deuterium.

6. The compound of claim 1 wherein $Y^2$ is hydrogen.

7. The compound of claim 1 wherein —CZ(R$^3$)$_2$ is —C(CH$_3$)$_3$ or —C(CD$_3$)$_3$.

8. The compound of claim 7, wherein —CZ(R$^3$)$_2$ is —C(CD$_3$)$_3$.

9. The compound of claim 1 wherein —CZ(R$^3$)$_2$ is —C(CD$_3$)$_2$OH.

10. The compound of claim 1 wherein —CZ(R$^3$)$_2$ is —C(CH$_3$)$_2$OH.

11. The compound of claim 2, wherein $Y^{1a}$ and $Y^{1b}$ are the same; $Y^2$ is hydrogen; and —CZ(R$^3$)$_2$ is —C(CH$_3$)$_3$ or —C(CD$_3$)$_3$.

12. The compound of claim 1 wherein $Y^2$ is hydrogen; —CZ(R$^3$)$_2$ is —C(CD$_3$)$_3$; and the compound is selected from any one of the compounds set forth in the table below

| Compound | R$^1$ | Y$^{1a}$ | Y$^{1b}$ |
|---|---|---|---|
| 101 | CH$_2$CH$_3$ | D | D |
| 102 | CH$_2$CH$_3$ | H | H |
| 103 | CH$_2$CD$_3$ | H | H |
| 104 | CH$_2$CD$_3$ | D | D |
| 105 | CD$_2$CD$_3$ | H | H |
| 106 | CD$_2$CD$_3$ | D | D |
| 107 | CD$_2$CH$_3$ | H | H |
| 108 | CD$_2$CH$_3$ | D | D | or a pharmaceutically acceptable salt of any of the foregoing.

13. The compound of claim 1 wherein $Y^2$ is hydrogen; —CZ(R$^3$)$_2$ is

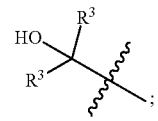

and the compound is selected from any one of the compounds set forth in the table below

| Compound | R$^1$ | R$^3$ | Y$^{1a}$ | Y$^{1b}$ |
|---|---|---|---|---|
| 201 | CH$_2$CH$_3$ | CD$_3$ | D | D |
| 202 | CH$_2$CH$_3$ | CD$_3$ | H | H |
| 203 | CH$_2$CD$_3$ | CD$_3$ | H | H |
| 204 | CH$_2$CD$_3$ | CD$_3$ | D | D |
| 205 | CD$_2$CD$_3$ | CD$_3$ | H | H |
| 206 | CD$_2$CD$_3$ | CD$_3$ | D | D |
| 207 | CD$_2$CH$_3$ | CD$_3$ | H | H |
| 208 | CD$_2$CH$_3$ | CD$_3$ | D | D |
| 209 | CH$_2$CH$_3$ | CH$_3$ | D | D |
| 210 | CH$_2$CH$_3$ | CH$_3$ | H | H |
| 211 | CH$_2$CD$_3$ | CH$_3$ | H | H |
| 212 | CH$_2$CD$_3$ | CH$_3$ | D | D |
| 213 | CD$_2$CD$_3$ | CH$_3$ | H | H |
| 214 | CD$_2$CD$_3$ | CH$_3$ | D | D |
| 215 | CD$_2$CH$_3$ | CH$_3$ | H | H |
| 216 | CD$_2$CH$_3$ | CH$_3$ | D | D | or a pharmaceutically acceptable salt of any of the foregoing.

14. A compound of claim 1 selected from 109 and 110:

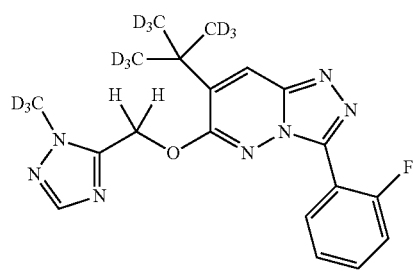

109

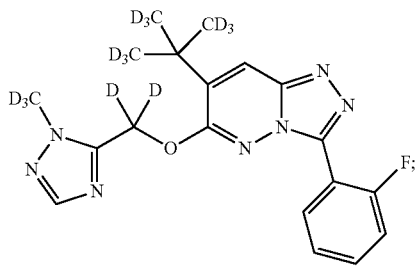

110 or a pharmaceutically acceptable salt of the foregoing.

15. The compound of claim 1 wherein any atom not designated as deuterium in any of the embodiments set forth above is present at its natural isotopic abundance.

16. A pyrogen-free pharmaceutical composition comprising a compound of claim 1 or a pharmaceutically acceptable salt of said compound; and a pharmaceutically acceptable carrier.

* * * * *